US010060567B2

(12) United States Patent
Van Nie et al.

(10) Patent No.: US 10,060,567 B2
(45) Date of Patent: Aug. 28, 2018

(54) TOOL, METHOD, AND SYSTEM FOR IN-LINE INSPECTION OR TREATMENT OF A PIPELINE

(71) Applicant: Rontgen Technische Dienst B.V., Rotterdam (NL)

(72) Inventors: Ronald Antonie Van Nie, Rotterdam (NL); Ruud Evers, Rotterdam (NL); Gerrit Jan Droogers, Rotterdam (NL)

(73) Assignee: RONTGEN TECHNISCHE DIENST B.V., Rotterdam (NL)

( * ) Notice: Subject to any disclaimer, the term of this patent is extended or adjusted under 35 U.S.C. 154(b) by 364 days.

(21) Appl. No.: 14/714,913

(22) Filed: May 18, 2015

(65) Prior Publication Data
US 2015/0330551 A1 Nov. 19, 2015

(30) Foreign Application Priority Data
May 19, 2014 (NL) ...................................... 2012839

(51) Int. Cl.
*A61B 5/04* (2006.01)
*F16L 55/18* (2006.01)
(Continued)

(52) U.S. Cl.
CPC ............... *F16L 55/18* (2013.01); *F16L 57/00* (2013.01); *F16L 58/04* (2013.01); *G01N 29/043* (2013.01);
(Continued)

(58) Field of Classification Search
CPC ........... G01N 29/265; G01N 2291/044; G01N 29/11; G01H 3/00; F16L 55/18; F16L 57/00; F16L 55/265; F16L 55/38
(Continued)

(56) References Cited

U.S. PATENT DOCUMENTS 4,641,529 A * 2/1987 Lorenzi ................ G01N 29/265
73/601
4,769,598 A * 9/1988 Krieg .................. G01N 29/2412
324/219
(Continued)

FOREIGN PATENT DOCUMENTS

EP 0 474 233 A1 3/1992
EP 1 618 831 A2 1/2006
(Continued)

OTHER PUBLICATIONS

Magne Andreas Vik et al., "Multi-Diameter, Bi-Directional Pigging for Pipeline Pre-Commissioning" XP055142766, Dec. 4, 2009.
(Continued)

*Primary Examiner* — Harshad R Patel
*Assistant Examiner* — Nigel Plumb
(74) *Attorney, Agent, or Firm* — Jacobson Holman, PLLC.

(57) ABSTRACT

A tool, method, and system for in-line inspection or treatment of a pipeline, with the tool including a first traction module on a first longitudinal end, and a second traction module on a second end. The tool includes at least one work module, such as an encoder module and/or an ultrasonic testing module, which is positioned between the first and second traction modules. A plurality of flexible connecting elements each interconnect one of the first and second traction modules for articulation to the at least one work module. Each of the first and second traction modules has at least one sealing element that causes propulsion in response to a fluid flow in a pipeline to be inspected or treated in one direction and allows relatively unhindered passing of the fluid flow in an opposite direction.

43 Claims, 11 Drawing Sheets

(51) Int. Cl.
  *F16L 57/00* (2006.01)
  *F16L 58/04* (2006.01)
  *G01N 29/04* (2006.01)
  *G01N 29/22* (2006.01)
  *F16L 55/26* (2006.01)
  *F16L 55/38* (2006.01)
  *F16L 55/40* (2006.01)
  *F16L 101/30* (2006.01)

(52) U.S. Cl.
  CPC .......... *G01N 29/225* (2013.01); *F16L 55/265* (2013.01); *F16L 55/38* (2013.01); *F16L 55/40* (2013.01); *F16L 2101/30* (2013.01); *G01N 2291/0234* (2013.01); *G01N 2291/0258* (2013.01); *G01N 2291/02854* (2013.01); *G01N 2291/044* (2013.01); *G01N 2291/2636* (2013.01)

(58) Field of Classification Search
  USPC .......... 73/623, 622, 620, 618, 596, 584, 570
  See application file for complete search history.

(56) References Cited

U.S. PATENT DOCUMENTS

| | | | | |
|---|---|---|---|---|
| 4,964,059 A * | 10/1990 | Sugaya | .................. | G01B 17/04 702/38 |
| 5,174,164 A * | 12/1992 | Wilheim | ............... | F22B 37/003 324/220 |
| 5,398,560 A * | 3/1995 | Zollingger | ........... | G01N 27/902 324/220 |
| 6,404,189 B2 * | 6/2002 | Kwun | .................... | G01N 22/00 324/220 |
| 6,772,637 B2 * | 8/2004 | Bazarov | ................ | G01M 3/005 73/623 |
| 7,111,516 B2 * | 9/2006 | Bazarov | ................ | G01B 17/02 73/623 |
| 7,900,517 B2 * | 3/2011 | Chougrani | ........... | G01N 29/043 73/592 |
| 7,950,284 B2 * | 5/2011 | Dijkstra | ............... | G01N 29/225 73/600 |
| 2008/0236287 A1 * | 10/2008 | Van Agthoven | ....... | G01N 29/07 73/623 |
| 2010/0199767 A1 * | 8/2010 | Ganin | .................. | G01N 29/225 73/623 |

FOREIGN PATENT DOCUMENTS

| | | |
|---|---|---|
| EP | 2 085 155 A1 | 8/2009 |
| EP | 2 623 840 A2 | 8/2013 |
| GB | 2 301 414 A | 12/1996 |

OTHER PUBLICATIONS

Jamal Al Amari et al., "SPE 49508 Bi-Directional I Ntelligent P Igging of 48 Inch Loading L Ine—ZADCO Experience", XP055143918, Jan. 1, 1998.

* cited by examiner

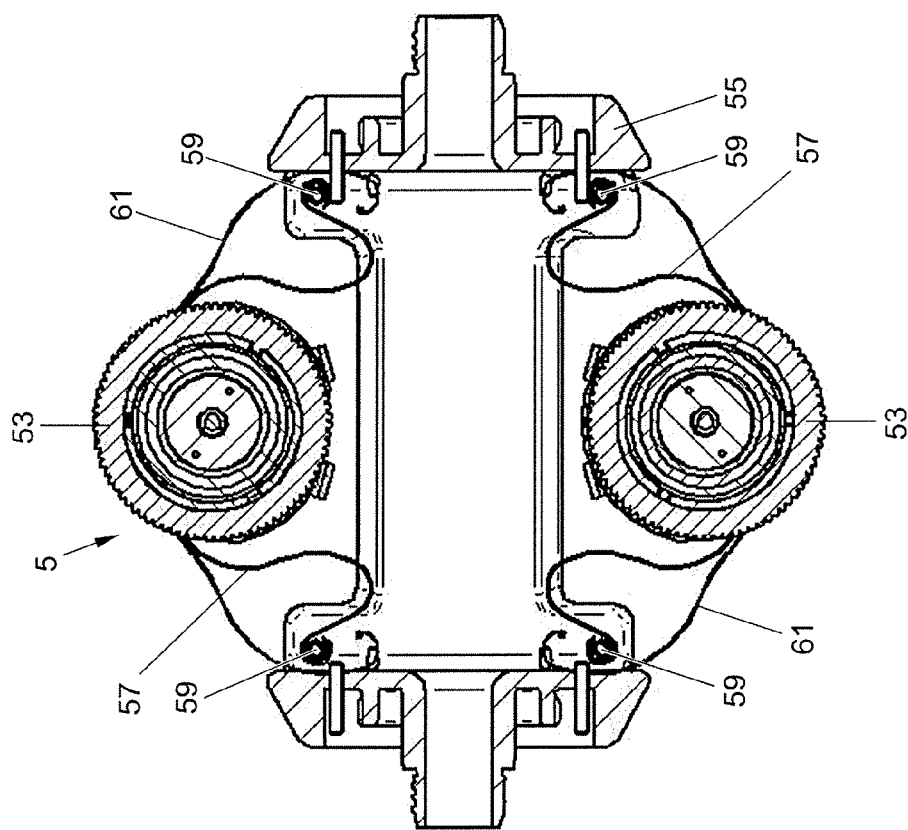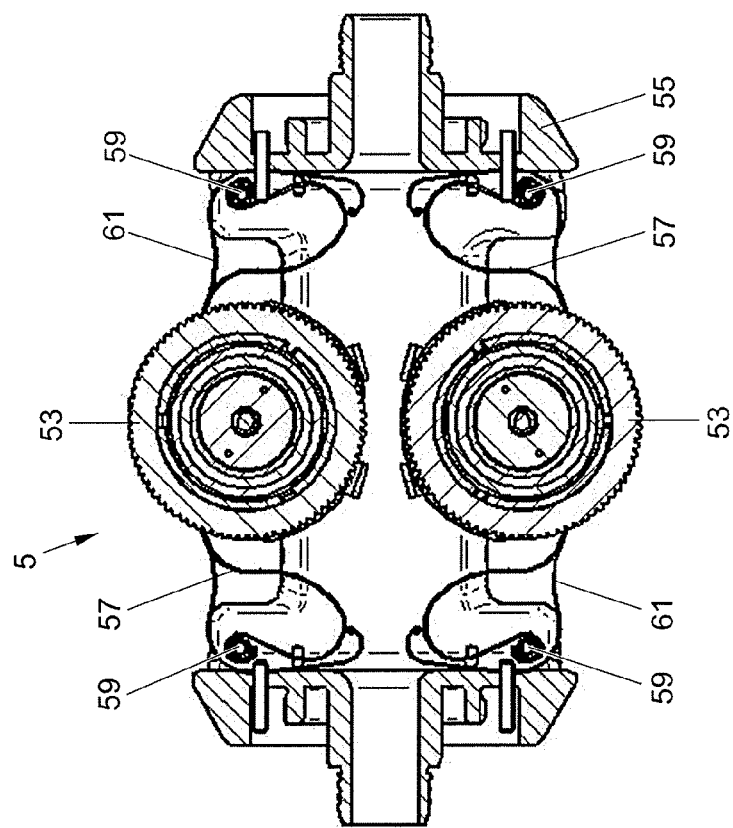

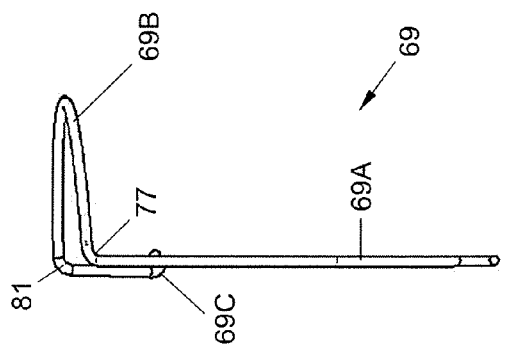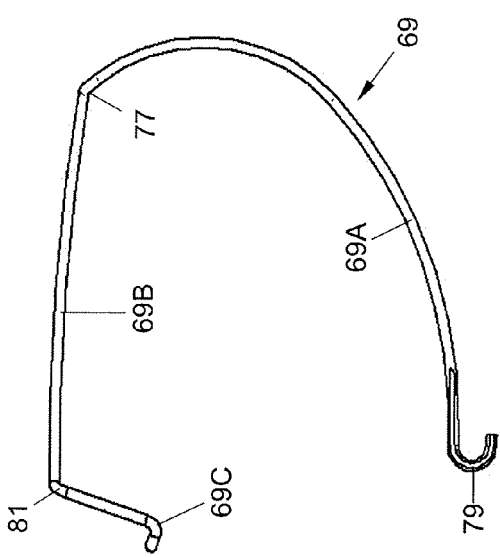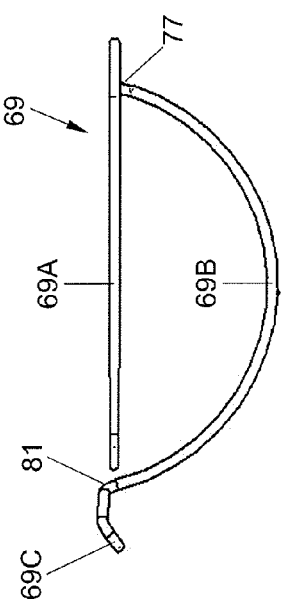
FIG. 11C
FIG. 11A
FIG. 11B

TOOL, METHOD, AND SYSTEM FOR IN-LINE INSPECTION OR TREATMENT OF A PIPELINE

The invention relates to a tool for in-line inspection or treatment of a pipeline, a method of inspecting or treating a pipeline, and a pipeline system including the tool for performing the method.

BACKGROUND OF THE INVENTION

Many pipelines for transport of oil and gas are not directly accessible for inspection because they are buried (on shore) or submerged (off shore). Several tools are available for In-Line-Inspection (ILI) of pipelines with a diameter of e.g. 16", 24" or larger. Also for smaller diameter pipes tools are available, like 4", 8" or 12", but these have limited capabilities. These tools perform ultrasonic, magnetic or eddy current examination of a pipe from the inside and are often referred to as 'pigs'. The collected data is used for assessment of the integrity and fitness for service of the pipeline.

In general the following criteria identify pipes which are difficult to inspect, especially in combination:
 small diameter (less than 200 mm diameter);
 multiple diameter;
 small radius bends (R=1D);
 back-to-back bends;
 T-junctions (in an ongoing direction);
 bore restrictions (weld roots, reducers, dents, valves);
 single access only (bi-directional movement of inspection tool required);
 short lengths, which make it difficult to control speed of inspection tool; and/or
 low pressure or low flow.

Obviously, smaller diameter pipes are more difficult to inspect from the inside because the inspection tool, including sensors, electronics and mechanics, must fit inside the pipe diameter. As stated above such tools are mainly available for larger diameter pipes like 16", 24" or 48" diameter or have limitations for the smaller diameters.

A pipe bend is classified according to the centerline radius (CLR) of the bend as a ratio to the nominal pipe diameter. For example an 8" N.P.S. pipe that is bent on a 12" CLR is classified as a 1.5D bend or 1.5 times the nominal pipe diameter (D). The abbreviation N.P.S. denotes Nominal Pipe Size, which is a North American set of standard sizes for pipes. It should be noted in this regard that the curvature of the CLR is the same for all 8" 1.5D bends, independent of the wall thickness or schedule of the pipe. Pipe schedules are defined in ASME B36.10 as predetermined relationships between pipe diameter and wall thickness. Depending on the situation the radius of curvature (R) of the bends can be large (only slightly bend), or 5D, 3D, 2D, 1.5D and even 1D (also named short radius bend).

In addition to the sharp curvature of bends, like in R=1D bends, also variations in diameters can exist. As stated above the relationship between diameters and wall thicknesses of pipes are standardized in schedules, depending on the required throughput and pressure. Originally, the outside diameter (OD) was selected so that a pipe, with a standard OD and a wall thickness suitable for a certain pressure, would have an inside diameter (ID) approximately equal to the nominal schedule size. Over time material and production technologies improved so it became possible to use thinner walls for the same pressure. In response to these developments the outside diameter of a particular pipe schedule was kept the same (to be able to fit new pipes to older existing pipe), but the inside diameter increased and is not anymore directly related to the pipe schedule. As a result not only the wall thickness depends on the working pressure but so does now the inner pipe diameter.

When the inner pipe diameter is accurately known then the tool can be adapted to that specific diameter before its introduction into the pipe, although it requires more preparation (time, components) to adapt the tool to an exact diameter. However, the exact inner pipe diameter may not always be known accurately, for example for older installations. In addition, if only a single pipe schedule is used for a complete installation and this pipe schedule is known then still variations in inner pipe diameter can occur because of manufacturing tolerances on the wall thickness (typically up to ±12.5%) and the outer diameter (typically ±1%). Taking these tolerances into account, the inner diameter of a 6" pipe can for example vary from 116 mm (schedule XXS) to 157 mm (schedule 40). The inner diameter of an 8" pipe can for example vary from 166 mm (schedule XXS) to 207 mm (schedule 40). It will be clear that the deviations allowed by the pipe schedule on the internal diameter have a stronger impact on smaller diameter sizes. Also, the inner pipe diameter may vary over the entire installation, resulting from variations in schedule due to different design pressures for different parts of the installation.

A significant part of pipeline failures (possibly more than 50%) are related to difficult to inspect pipe segments with available pigging tools, hence these pipelines are often referred to as 'difficult to pig pipelines' or even 'unpiggable pipelines'. New technologies are required to deliver measurement data of such pipes to be able to perform assessment and maintenance planning. The examination may include a high resolution ultrasonic pipe wall survey, for determining the thickness of the pipe wall or detection and sizing of cracks in the pipe wall and/or determining deformations (dents), followed by engineering evaluation of the data and recommendations regarding the continued operation of the pipeline segment. Depending on the purpose of the survey the coverage may include straight pipe segments, welds between pipe segments or other parts of the pipe.

To overcome these issues it is preferred that the tool is capable of covering a certain range of pipe inner diameters without modification of the tool. Hence a free-floating in-line wall-thickness or crack detection inspection system for small diameter, unpiggable pipelines is required, which provides full coverage and high sensitivity (detection of 'small' defects) in small diameter pipes having sharp bends (R=1D, over 180°). Often such installations have barred and unbarred off-takes (T's, branch). The tool must be capable of operating in both directions (mechanically and measurement) with high resolution at a high speed, for example 1 m/s. Data storage capacity must be suitable for pipe lengths of several kilometers.

BRIEF SUMMARY OF THE INVENTION

Accordingly it is an object of the present invention to propose an improved free-floating, modular ILI-tool. The design parameters for an improved tool, method, and system for in-line inspection or treatment of a pipeline include inspection maneuverability requirements (pipeline diameter, length, curvature, etc.), trade-offs between scanning accuracy and speed, and required support systems (launch or retrieval, free-floating or tethered, etc.). The design criteria for the tool and system that are important to quality include:
 Free floating;
 Single point pipeline access;

Capability of maneuvering through consecutive R=1D bends;

Capability of accurate wall thickness and/or crack measurements;

Having a high scanning resolution;

Full coverage, at least in straight pipe segments;

Having a high inspection speed, balanced with resolution; and/or

Inspection results stored for further analysis.

In a more general sense it is thus an object of the invention to overcome or reduce at least one of the disadvantages of the prior art. It is also an object of the present invention to provide alternative solutions which are less cumbersome in assembly and operation and which moreover can be made relatively inexpensively. Alternatively it is an object of the invention to at least provide a useful alternative.

To this end the invention provides for a tool, method, and system for in-line inspection or treatment of a pipeline as defined in one or more of the appended claims. The tool, method, and system according to the invention in at least one of its embodiments offers:

full coverage (circumferential+axial) in straight pipe segments with static probe head;

free floating (no cable, no motor traction, on-board data storage, off-line evaluation); and bi-directional ability (tool and measurement).

The In-Line Inspection (ILI) according to the invention also provides an alternative to hydrostatic testing for periodic qualification of pipe integrity as required by regulation (compliance) which only provides general, not localised, information. In addition, the data from ILI can be used to manage immediate integrity as well as future integrity (integrity management). Advantages of using ILI tools for pipeline inspection include:

complete survey of the pipe wall (inclusive of metal loss, denting, possible cracking; and auditable data);

speed of operation;

accurate positioning of defects; and/or less disruption to land owners.

Data retrieved from the on-board data storage can be subjected to a computer implemented processing and analyzing of the collected and recorded data to determine and identify locations of the pipeline in need of immediate or future treatment.

BRIEF DESCRIPTION OF THE SEVERAL VIEWS OF THE DRAWINGS

Further advantageous aspects of the invention will become clear from the appended description and in reference to the accompanying drawings, in which:

FIG. 8A is a simplified longitudinal cross section of the encoder of FIG. 7 showing the encoder wheels in a retracted position;

FIG. 8B is a simplified longitudinal cross section as in FIG. 8A, but showing the encoder wheels in an extended position;

FIGS. 11A to 11C are different views of a single centering spring as used in the ultrasonic testing module of FIGS. 9 and 10.

DETAILED DESCRIPTION OF THE INVENTION

Figure 1:
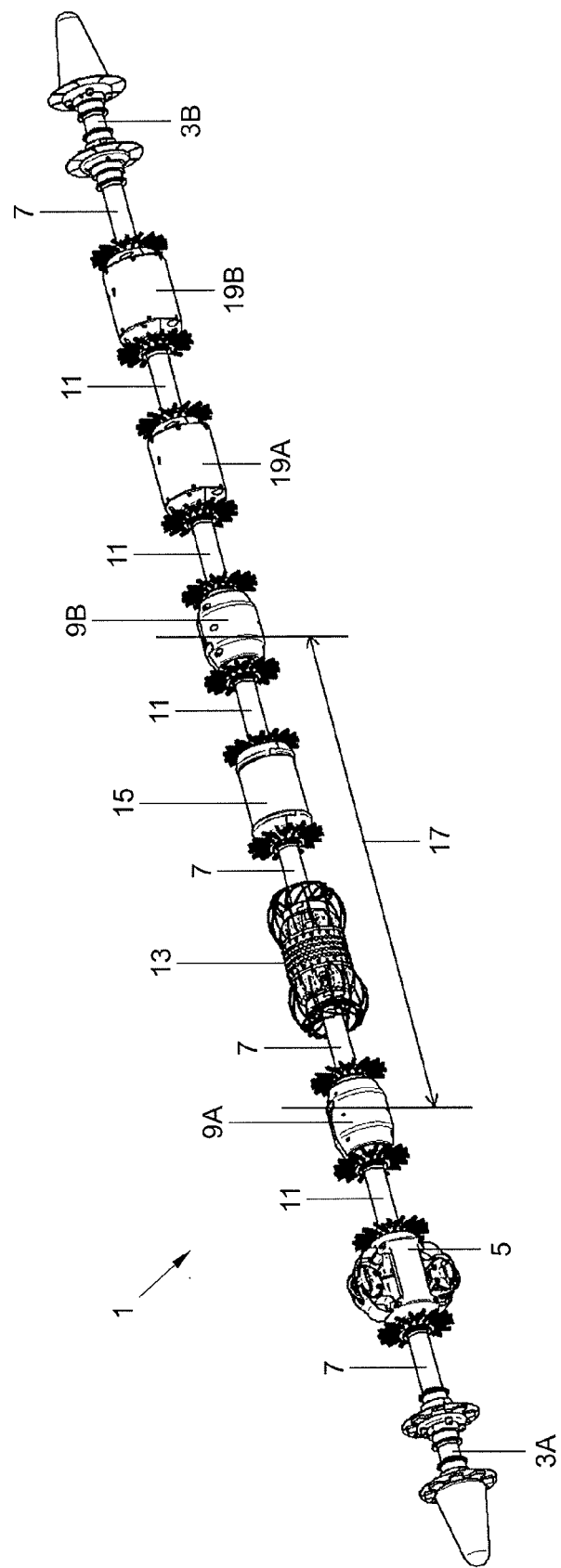
FIG. 1 is a perspective view of a main assembly of a tool in accordance with the invention.

Referring to FIG. 1 a main assembly of a tool 1 is shown. In FIG. 1 a main assembly of a tool 1 for in-line inspection of a pipeline is shown. Starting from the left hand side of FIG. 1 a first traction module 3A is followed by an encoder module 5. The encoder module 5 is flexibly connected to the first traction module 3A in an articulated fashion by a first type of flexible connection element 7. The encoder module 5 is followed by a first connector module 9A, which in turn is connected to the encoder module 5 through a second type of flexible connecting element 11. The second type of flexible connecting element 11 differs from the first type of flexible connecting element 7 in having a bristle at each of its opposite longitudinal ends. The first type of flexible connecting element 7 only has a bristle on one of its longitudinal ends. The first connector module 9A accommodates electrical connection and forms a barrier between oil filled pressure compensated modules and non-pressure compensated modules and ditto flexible elements, as will be explained below. The first connector element 9A is followed by an ultrasonic testing module 13 and connected thereto by a first type of connecting element 7. The ultrasonic testing module 13 can accommodate transducers and multiplexers to the extend that is necessary.

On an opposite longitudinal end the ultrasonic testing module 13 is coupled through another first type of connecting element 7 to an electronics module 15.

The electronics module 15 can accommodate any combination of a pulser, receiver, digitizer and data storage, as known to the skilled person. Through a further second type of connecting element the electronics module 15 is coupled to a second connector module 9B. The second connector module 9B will also accommodate electrical connections and form a barrier for oil filled pressure compensated modules and flexible connecting elements. Accordingly a pressure compensated section 17 is defined between the first and second connector modules 9A, 9B. Following the second connector module 9B and connected thereto by a second type of connecting element 11, is a first battery module 19A. The first battery module 19A in this example is followed by a second battery module 19B, also connected to the first battery module 19A by a second type of connecting element 11. The number of battery modules 19A, 19B is optional, but would normally depend on the length of pipeline to be inspected by the tool 1. The second battery module 19B is followed by a second traction module 3B. The second traction module 3B is in an inversed position with respect to the first traction module 3A, and is connected by a first type of flexible connecting element 7 to the second battery module 19B. Data retrieved from the on-board data storage of the electronics module 15 will be subjected afterwards to a suitable computer implemented processing and analyzing to determine and identify locations in the pipeline in need of immediate or future treatment.

Thus the tool 1 includes individual bodies that each has a specific function. In the main assembly of FIG. 1 the following modules are shown, from left to right:

first traction module 3A;
encoder module 5;
connector module 9A (acting as pressure compensation barrier);
ultrasonic testing module 13 (inclusive of any transducers, multiplexers);
electronics module 15 (inclusive of any pulser, receiver, digitizer, data storage);
connector module 9B (acting as pressure compensation barrier);
two battery modules 19A, 19B;
second traction module 3B (for traction in an opposite direction); and
several interconnections between modules, elements 7 and 11.

The individual bodies other than traction modules and interconnections will be referred to herein as 'work modules'.

The ultrasonic testing module 13 and the electronics module 15 are pressure compensated, meaning that they are filled with oil and that the external pressure (pressure of the fluid in the pipe) is passed to the oil inside the pressure compensated modules. The interconnections (connecting elements 7 or 11) between these modules 13, 15 and the interconnections to the connector modules 9A, 9B are pressure compensated and filled with oil, as well as part of each connector module. Pressure compensation allows for using thinner and lighter module bodies, decreasing the weight of the tool (closer to neutral buoyancy) and hence reducing friction of the parts in contact with the pipe inner surface. It is advantageous to keep the oil in the pressure compensated parts separated from the fluid in the pipe, to prevent leakage and to prevent contamination of the oil inside the modules (e.g. dirt, water).

The battery modules 19A, 19B are not filled with fluid but have a housing, conveniently made of metal, that can resist the pressure in the pipe. To prevent that fluid in the pipe leaks into the housing of the battery modules the electrical connections through the housing (cables, connectors) must be pressure resistant as well. To enable switching off the battery power from the external electrical connections, e.g. for safety during shipment of the tool, without opening the pressure resistant housing and without pressure resistant switch through the housing a reed-relay inside the housing is activated from outside the housing. The material of the housing is preferably aluminum or stainless steel to enable the use of an external magnet to activate the reed-relay, alternatively the housing could be made of plastic suitable for the pressure inside the pipe. The interconnections (connecting elements) to the battery modules, the interconnections (connecting elements) to the encoder module 5 and the encoder module itself are not pressure compensated. In fact, the interconnections and modules that are not pressure compensated and are not pressure resistant can be open to allow the fluid inside the pipe to enter into these interconnections or modules. In FIG. 1 the pressure compensated section between connector modules 9A and 9B is indicated by arrowed line 17.

The dimensions of the modules are limited due to the inner pipe diameter and the curvature of the bends, as will be explained below.

Figure 2:
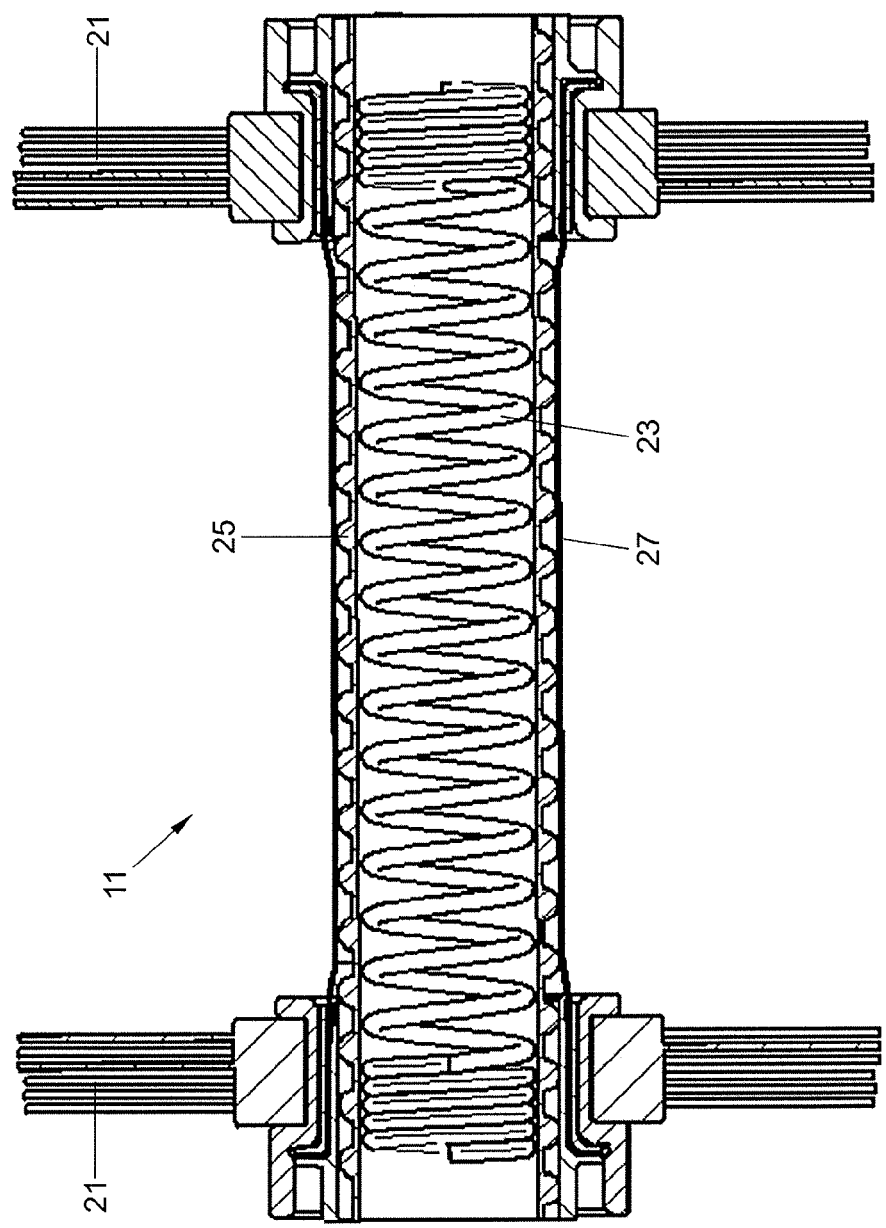
FIG. 2 shows a partial cross section of a flexible connecting element suitable for use in the tool of FIG. 1.

FIG. 2 shows in cross section one of the connecting elements for interconnection of the various work modules. The flexible connecting element 11 shown in FIG. 2 is of the second type with bristle 21 on opposite longitudinal ends. An internal helical spring 23 is surrounded by a tubular elastomeric cover 25. The tubular cover 25 is protected by a woven or braided metal outer sheet 27.

All interconnections between the modules (connecting elements 7 and 11) are flexible. These flexible interconnections include an internal helical spring 23, a plastic or rubber cover or tube 25 (for the pressure compensated interconnections) and a woven or braided metal protection 27.

After passing the bend the helical spring 23 aligns the modules into a straight position again. The helical spring 23 also prevents the interconnection from collapsing and thus protects the cables inside.

The interconnections in particular include:

A stainless steel spring 23, helically shaped. This spring prevents sharp bending of the interconnections (elements 7 or 11) to protect cables inside. In addition, this spring has a preferential straight position which helps to align the modules after passing a bend. This spring 23 is not strong enough to transfer the pulling force.

Rubber hose 25 for sealing the contents of the interconnection, to prevent entrance of dirt etc., but still allows for pressure compensation between the outside and inside. The rubber hose 25 is optional in interconnections without a cable, such as in the traction module 9A, 9B.

Metal protection 27 of woven steel, which transfers the pulling force from one module to the next module. It also provides mechanical protection of the rubber hose 25, if present.

The modules are associated with bristles 21 on the interconnections for substantial centralized positioning, except for the traction modules 9A, 9B and the ultrasonic module 13, while limiting the amount of friction. Together with the low weight of the tool 1, preferably close to neutral buoyancy, this allows for low pressure and low flow use. Also, the low weight of the tool requires only relative soft bristles or springs.

The electronics module 15 is only partly covered by a plastic protection cover, so its metal body is, at least partly, in contact with the fluid medium to allow for better heat transfer to prevent high temperatures inside the electronics module 15.

It is known that a relatively rigid body must meet certain geometrical requirements to be able to move through a bend. Especially the relation between length and diameter of the body, or the distance and diameter of parts in contact with the inner surface of a pipe, such as discs or bristles, are important in view of the diameter and curvature of the pipe. In addition the connections to other bodies or modules can influence the position and behavior in bends.

Figure 3:
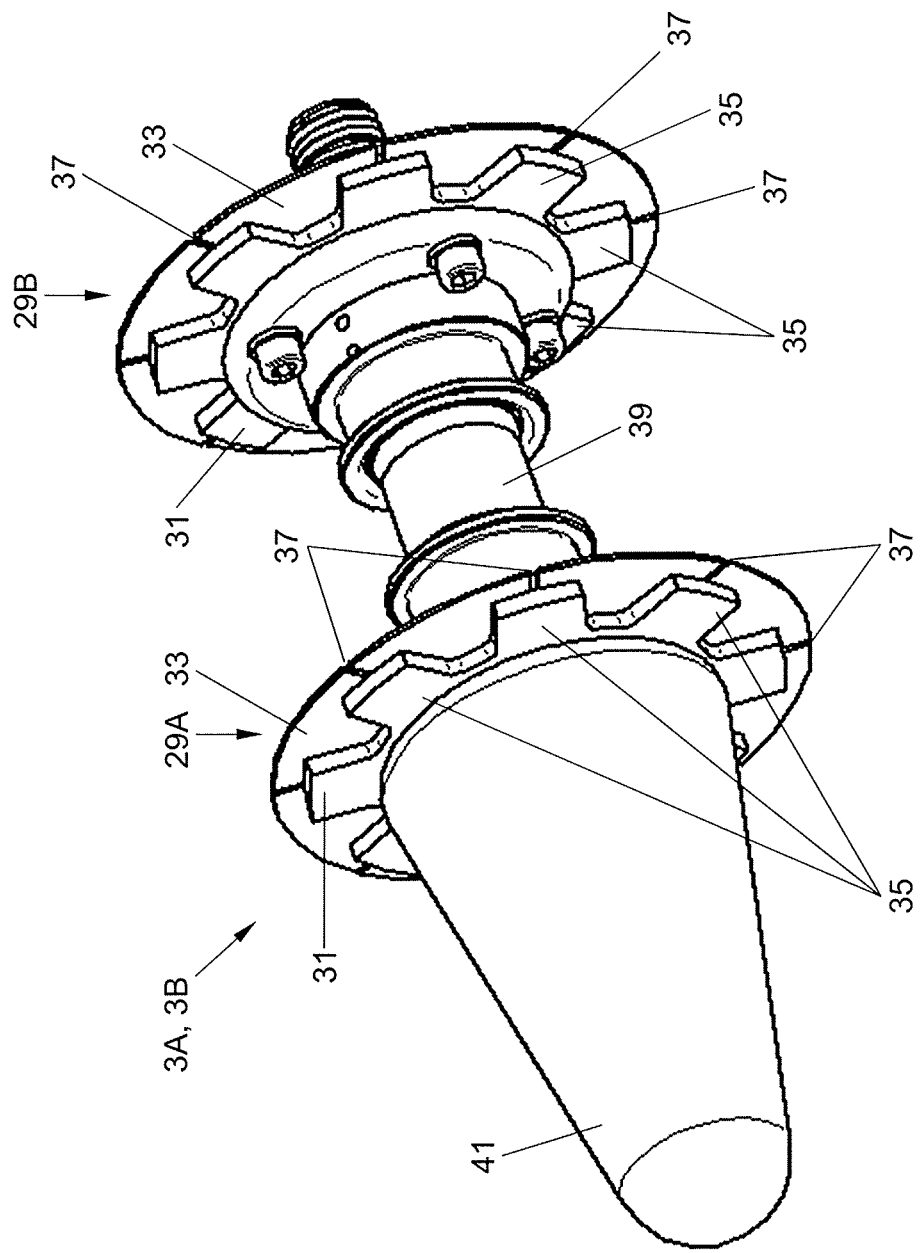
FIG. 3 is a perspective view of a traction module suitable for use in the tool of FIG. 1.
Figure 4:
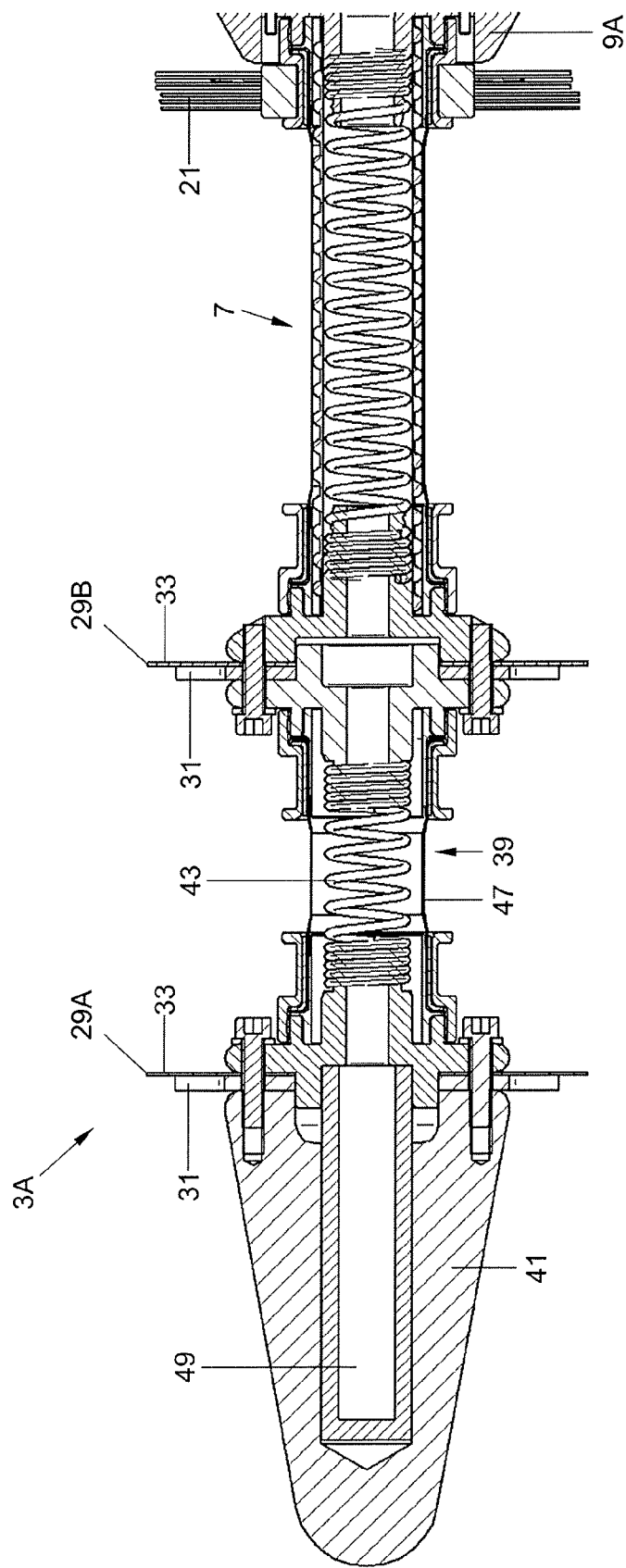
FIG. 4 is a partial view of a longitudinal cross section of a forward end of the tool of FIG. 1.
Figure 5:
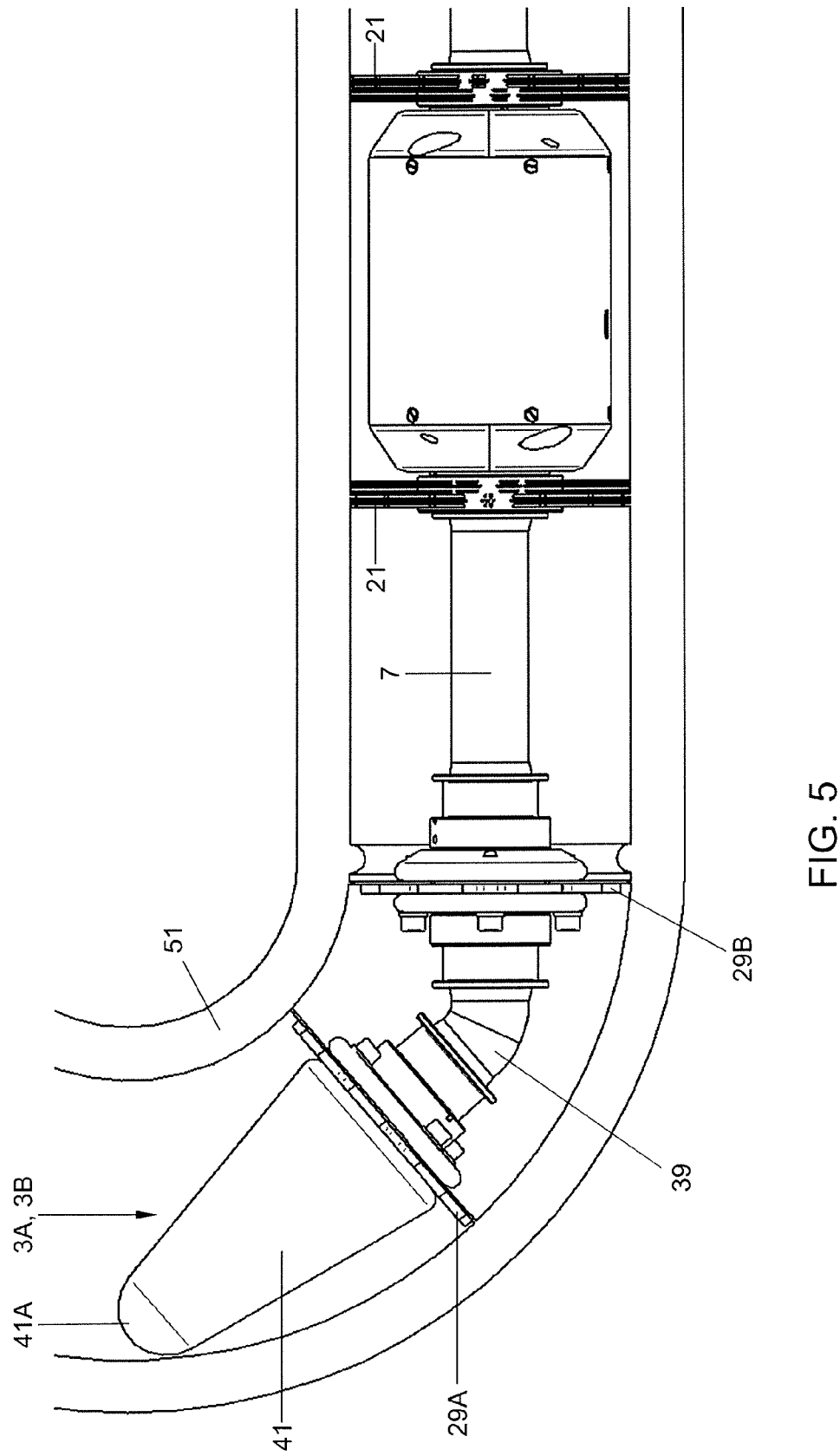
FIG. 5 shows a forward end of the tool of FIG. 1 in a pipe bend.

FIGS. 3 to 5 show the traction module in more detail. The traction module shown in FIG. 3 is representative for either of the first and the second traction modules 3A, 3B. Hence the description relates to each of these and the constituting elements are identical. Traction module 3A, 3B as shown in FIG. 3 includes a first set of flap-like discs 29A and a second set of flap-like discs 29B. Each of the first and second sets of discs 29A, 29B has a relatively rigid disc 31 and a relatively flexible disc 33. The relatively rigid disc 31 is of an equal or a smaller diameter than the relatively flexible disc 33 and has a plurality of radially extending tongues 35. The radially extending tongues 35 of the relatively rigid disc 31 are positioned to cover radially extending slits 37 in the relatively flexible discs 33. The second set of discs 29B is positioned at a distance from the first set of discs 29A by a flexible interconnection 39 which is somewhat similar in construction to the first and second types of connecting elements described above. This means, as will be further explained below, that the second set of discs 29B is flexibly articulated to the first set of discs 29A. An outermost longitudinal end of the traction module 3A, 3B is provided with a nose cone 41 for a purpose that will be described below.

A longitudinal cross section of the first traction module 3A in FIG. 4 reveals that the flexible interconnection 39 that spaces and flexibly connects the first and second sets of discs 29A, 29B is also composed of an inner helical spring 43 and a woven or braided metal protective sheet 47.

The first and second sets of discs 29A, 29B are kept at a distance which substantially corresponds to the diameter of the first and second sets of discs 29A, 29B. This ensures that traction by fluid flow is maintained when passing pipe junctions, such as when passing a barred or unbarred T-section.

The nose cone 41 as shown in FIG. 4 can have a hollow interior 49 that may be used for housing electrical components, when applicable.

The traction module includes two sets of flap-like discs 29A, 29B. In the present embodiment each set of discs contains two discs: a relatively rigid disc 31 and a relatively flexible or soft disc 33. The relatively rigid disc 31 provides support to keep the traction module 3A, 3B somewhat centralized inside a pipe. It is to be understood that relatively rigid does not necessary mean solid so it can have some flexibility but less than the relatively soft discs 33, the relatively rigid discs 31 are able to support the weight of the module, in this case the traction module 3A, 3B. It is known, that flexibility not only depends on the material properties but also on the thickness in which it is used. The relatively rigid disc 31 and the relatively soft disc 33 could thus, for example, also be made of the same material but have different thicknesses. The flexible disc 33 is positioned on the side of the relatively rigid disc 31 that is closest to the other individual bodies (such as interconnections and work modules), and may comprise 'leafs' separated by slits 37. If the fluid flow enters from the front of the traction module 3A, 3B then the flexible disc 33 will bend away from the relatively rigid disc 31, allowing the fluid to pass by without causing substantial force on the traction module 3A, 3B. On the other hand, if the fluid flow enters from the work module side of the traction module 3A, 3B then the flexible disc 33 will be pushed against the relatively rigid disc 31 and substantially seal of the complete cross section of the pipe, causing the fluid flow to push the traction module 3A, 3B forward.

As an example, the distance between the sets of discs 29A, 29B of a traction module 3A, 3B can, by way of example, be 115 mm while the relatively rigid discs can be 124 mm in diameter.

For moving the tool through a pipe a fluid flow is created in the pipe (by an external pump system not shown, but conventional). The flexible discs 33 of the second traction module 3B at the rear side of the tool will open and let the fluid pass by. The flexible discs 33 of the first traction module 3A at the front side of the tool will close and cause a force that moves the tool 1 through the pipe in the direction of the fluid flow. A pulling force only at the front end traction module 3A is advantageous because then the other modules of the tool 1 are pulled (drawn, towed) through the pipe, resulting in a more controlled and stable movement and better alignment with the longitudinal pipe axis. It must be noted that a pushing force at the rear end of the tool 1 could result in the modules to hinge (bind, clog, constipate) resulting in poor alignment.

When the fluid flow is reversed then the flexible discs 33 will work the other way around, still providing a traction force only at the traction module 3B at the end of the tool in the direction of the intended movement. In this way a bi-directional tool can be moved through the pipe in both directions without external intervention by an operator or complex mechanical or electronic regulations in the tool, while maintaining suitable alignment and stable movement.

The diameters of the relatively soft or flexible and relatively rigid discs 33, 31 are selected depending on the pipe inner diameters to be examined and on the possibilities to regulate the fluid flow speed. In case the fluid flow speed does not exceed the preferred tool speed then the following applies:

The diameter of the relatively soft discs 33 should be as large as possible to use the fluid flow efficiently for traction. However, using relatively soft discs 33 that are larger than the inner diameter of the pipe causes the discs to touch or scrape the pipe inner surface, resulting in friction while traction is hardly improved. Therefore the preferred diameter of the relatively soft discs 33 is always equal to or smaller than the pipe inner diameter. More precisely, for situations where pipes of different diameter or schedules are tested, the relatively soft discs 33 shall be equal to or smaller than the largest or average inner diameter. This means that the relatively soft discs can be larger than the smaller inner diameters, the effect is described below.

It should be noted in this regard that if a certain amount of fluid is pumped through a series of pipes of different inner diameters then the resulting fluid flow speed is smaller in a pipe with a larger diameter, so proper traction is more important in a larger pipe.

The diameter of the relatively rigid discs 31 shall be smaller than the inner diameter of the pipeline to be examined to ensure that the traction unit can pass through the pipe without getting stuck or that the relatively rigid discs 31 cause too much friction. More precisely, for situations where pipes of different diameter or schedules are tested, the relatively rigid discs 31 shall be smaller than the smallest inner diameter. It should be noted in this regard that also obstacles, like weld root penetrations, must be taken into account for selecting the diameter of the relatively rigid discs 31, in combination with the limited flexibility of the relatively rigid discs, if applicable.

In case the relatively soft discs 33 are larger than the relatively rigid discs 31 and pipes of different diameter or schedules are tested, the relatively soft discs 33 of the front traction unit will touch or scrape the pipe inner surface for the smaller diameters. In case the friction could be too large compared to the traction, e.g. for very low flow speeds, the diameter of the relatively soft discs 33 should be reduced to be equal or smaller to the smallest internal diameter.

At the rear traction unit 3B a relatively soft disc 33 that is larger than the relatively rigid disc 31 could bend over the relatively rigid disc. To prevent the rear traction unit to get stuck and or to limit friction of the rear traction unit 3B to the inside pipe surface, the diameter of the relatively rigid discs 31 shall be smaller than the smallest inner pipe diameter reduced by the thickness of the relatively soft disc 33.

It should be noted in this regard that if the tool 1 is used in two directions the function of the two, first and second traction units (front and rear) will be reversed, so for bi-directional use the traction units should both meet the requirements described above.

In case the fluid flow speed inside pipes is higher than the preferred travelling speed of the tool (e.g. for complete coverage) and the fluid flow speed cannot be reduced then smaller discs or discs with intended leakage (e.g. holes) will result in less traction and hence a reduced tool speed. This is however not a relevant embodiment of the present invention.

It should be noted in this regard that the tool 1 will be moved by the fluid flow and no large pressure difference (0.5-1 bar) is required due to the low friction of the parts in contact with the pipe inner surface and the low weight of the tool, preferably close to neutral buoyance of the tool. The low weight and low friction also allows the tool to pass through inclined pipes using the fluid flow and no large pressure difference, such as in hilly terrain or even vertical pipes in installations, both uphill and downwards. Prior art tools may have discs or cups that substantially seal of the pipe cross section to generate traction but this typically leads to more friction and is typically suitable for moving the tool in one direction only.

It should be noted in this regard that only the ultrasonic module 13 needs to be accurately centralized for the measurement, however the other modules are also substantially centralized to prevent forces on the ultrasonic testing module 13.

In FIG. 5 a traction module 3A, 3B is shown in position in a pipe bend of a pipeline 51. It is thus seen that a radiussed tip 41A of the nose cone 41 contacts the inner surface of the bend's outer wall to thereby position the first set of discs 29A substantially perpendicular to the inner pipe wall in the bend. The flexible interconnection 39 allows for the second set of discs 29B to also remain substantially perpendicular to the inner wall of the pipeline 51 at the position where the second set of discs 29B is located. In the example of FIG. 5 the traction module 3A, 3B is connected to another module by means of a first type of connecting element 7.

The first and second traction modules 3A, 3B are provided with a nose cone 41 that is designed to follow the contour of sharp, small radius bends. By contact between the end of the nose cone and the bend the traction module 3A, 3B follows the curvature of the bend while the discs (sets 29A, 29B) stay substantially perpendicular to the pipe axis. Thereby the discs (sets 29A, 29B) are also approximately perpendicular to the pipe inner surface, which is important to cover most of the pipe cross section and use the fluid flow for moving the tool. The interconnection 39 between the sets of discs 29A, 29B is somewhat flexible to allow passing sharp, small radius bends while both sets of discs 29A, 29B stay substantially perpendicular to the pipe surface. This flexible interconnection 39 includes an internal helical spring 43, an optional plastic or rubber cover, such as a tube 45, and an advantageously woven metal protection 47. After passing the bend the helical spring 43 aligns the module 3A, 3B into the straight position again. Without the flexible part 39 between the sets of discs 29A, 29B the traction module 3A, 3B cannot pass sharp, small radius bends, due to the combination of distance between the sets of discs and the diameter of the relatively rigid discs. Alternative embodiments could contain a flexible joint or ball like hinge, however these typically are not inherently biased to return to a straight position after passing the bend which is a desirable additional requirement.

The length dimension of the cone 41 depends on the inner pipe diameter, or more particularly to a range of inner pipe diameters, and the curvature(s) of the bends.

Typically the bends in installations can have a radius of curvature as sharp as 1D, meaning that the radius of the bend (measured at the pipe axis) equals the diameter D of the pipe. The angle of the bends can be 180° (U bend), 90° single bend or 90° back-to-back (two bends of 90° directly connected). The 90° back-to-back bends can be in the same plane (forming an S bend or U bend) or be in different planes. Also smaller bends like 45° exists but these are less challenging and are considered not restricting if the 90° bends can be passed.

The length of the nose cone 41 also prevents that the tool enters into off-takes, such as T connections. As the tool mainly interacts with the outside surface of the bend, the length of the nose cone is preferably optimized for the curvature of the outside of the bend (at the inside surface of the pipe) for the most difficult situation, being a combination of:

The smallest nominal diameter (in the present example 6");
The sharpest bend (in the present example R=1D);
The smallest internal diameter (resulting from the maximum wall thickness).

Figure 6:
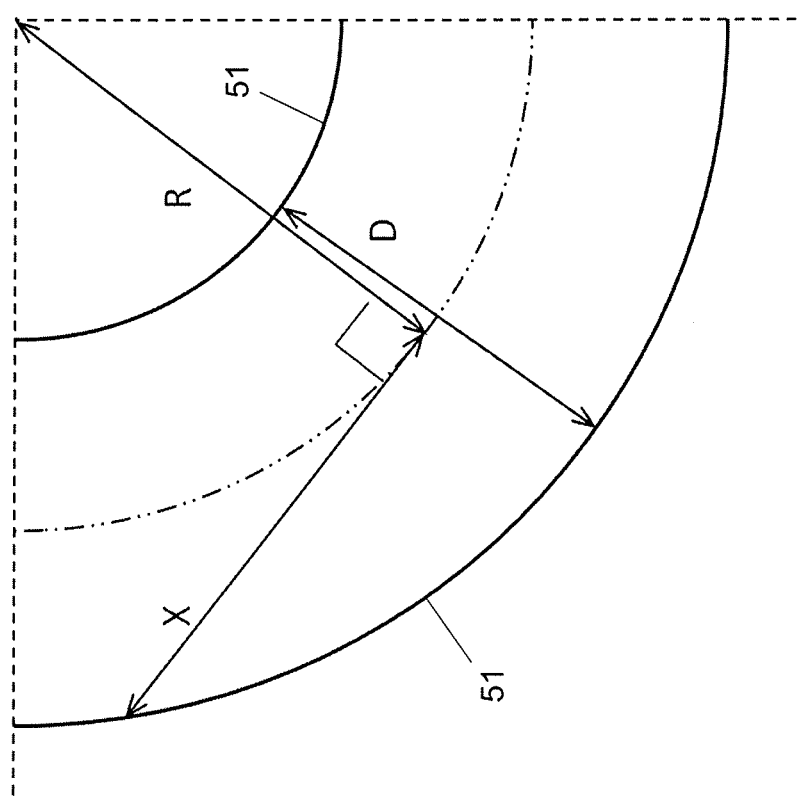
FIG. 6 is a schematic diagram showing a theoretical optimum nose length of a traction module in relation to pipe diameter and radius of pipe bend.

It was realized that not only the nominal diameter and the curvature (centerline radius, CLR) are important but also the internal diameter (depending on the wall thickness or schedule), see FIG. 6.

The diagram of FIG. 6 schematically shows the outline of a bend in a pipeline 51 and the relative positions of inner pipe diameter D, radius of curvature R, and optimum nose cone length X. The practical nose cone length can vary slightly from this theoretical optimum value while still performing well. However, the practical nose cone length must not be too long to be able to pass sharp bends. Therefore the optimum nose cone length is calculated for the sharpest bend (smallest curvature R). For less curvature situations (larger inside diameter, larger radius) the cone length will be somewhat less optimum, however the tool will pass through less curved bends more easily. Calculation of cone length X can be based on the diagram shown in FIG. 6. The preferred length of the cone can be determined or be calculated using basic goniometry, resulting in the formulas below:

$$X^2 + R^2 = (R + D/2)^2$$

$$X^2 = (R + D/2)^2 - R^2 = D^2/4 + R*D$$

$$X = \sqrt{(D^2/4 + R*D)}$$

R=centerline radius
D=inner diameter

The calculated length X obtained from this formula would be a theoretical optimum for a sharp, unrounded nose, whereas in practice a rounded tip 41A is preferred. The width of the rounded tip of the cone thus has to be taken into account as well (see traction module in bend as shown in FIG. 5) so the effective cone length in practice will be somewhat shorter than X. The skilled person will easily make the necessary adaptations and for a nominal 6" pipe diameter and radius of curvature (R=1D; internal diameter 116 mm) a cone length of 135 mm results, when the round tip of the cone has a radius of 20 mm. This equals a theoretically calculated optimum cone length of 145 mm according to the formula given above.

Optionally, the traction module 3A may also have a bristle. Optionally, an interior space in the nose cone 41 can be utilized for housing equipment 49, like a pinger for tool localization (conventional).

Due to the sharp, small radius curvature of the bends it is difficult to avoid that the outside of the tool modules contacts the surface of the pipe at bends, especially at the inside radius of the bend. Hence the tool is designed to withstand such contacts and still pass smoothly through the bends.

Figure 7:
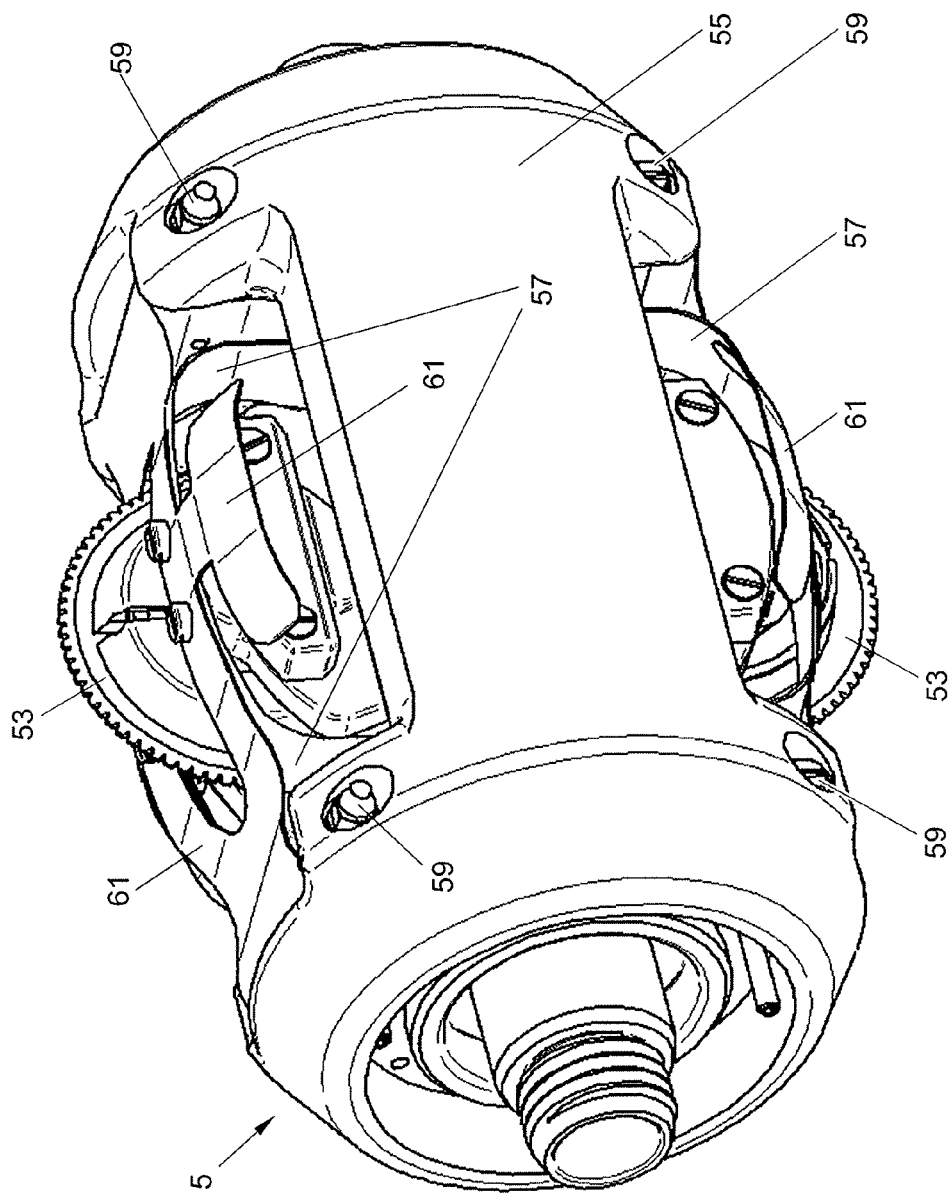
FIG. 7 is a perspective view of an encoder module suitable for use in the tool of FIG. 1.

The encoder module 5 is shown in greater detail in FIG. 7. The encoder module 5 is guided substantially centrally in a pipeline by the bristles of the flexible connecting elements on either side (not shown in FIG. 7, but shown in FIG. 1). To ensure proper operation of the encoder module over a wide range of inner pipeline diameters, two encoder wheels 53 are mounted opposite to one another at the circumference of a body 55 of the encoder module 5. The encoder wheels 53 are mounted on leaf-springs 57 having a special S-shape giving a radially outward bias to the encoder wheels 53 to ensure continuous contact with an inner pipeline surface. The leaf-springs 57 has opposite ends pivotally attached to the encoder body 55 by pivot pins 59 inserted into the encoder body 55. The outward bias of the encoder wheels 53 and leaf-springs 57 is further shown in FIGS. 8A and 8B, which will be further explained below. To prevent encoder wheels 53 from extending too deeply in to off-takes at pipe junctions and to prevent the encoder wheels 53 from getting stuck in such off-takes an additional covering leaf 61 is added to the leaf-springs 57, where the additional covering leaf 61 also extends laterally of the encoder wheel 53 as shown in FIG. 7.

Encoder module 5, wheels 53 are shown in an 'in' position (in a small diameter pipe, schematic position of encoder wheels in FIG. 8A) and an 'out' position (large diameter pipe, encoder wheels in FIG. 8B). The outer ends of the additional covering leaf 61 are preferably recessed into the body 55 of the encoder module 5 as also shown in FIG. 7. The particular S-shape of the encoder springs 57, for small diameter (FIG. 8A) and large diameter (FIG. 8B) is also visible in FIGS. 8A and 8B. It should again be noted in this regard that the outer ends of the additional covering leaf 61 as stated above are preferably recessed into the encoder module 5 and that the outer ends of the spring leaf 57 as stated above are pivotally mounted to pivot pins 59 inserted the body 55 of the encoder module 5 as shown in FIGS. 8A and 8B.

The wheels 53 of the encoder must be maintained in contact with the pipe inner surface at all times, independent of the diameter within a certain range. Two encoders 53 on opposite sides are used for better alignment of the encoder module 5 with the pipe axis. A second encoder also provides redundancy for the distance measurement. Due to the large variation in diameter the encoder wheels 53 must be able to travel over a long path (stroke) while maintaining a certain pressure. To solve this problem a dedicated spring 57 of double S shape is used. To prevent the encoder wheels 53 to enter into or get stuck in off-takes an additional covering spring leaf 61 is used. The encoder type is magnetic, and except the wheels 53 there are no moving parts.

Figure 9:
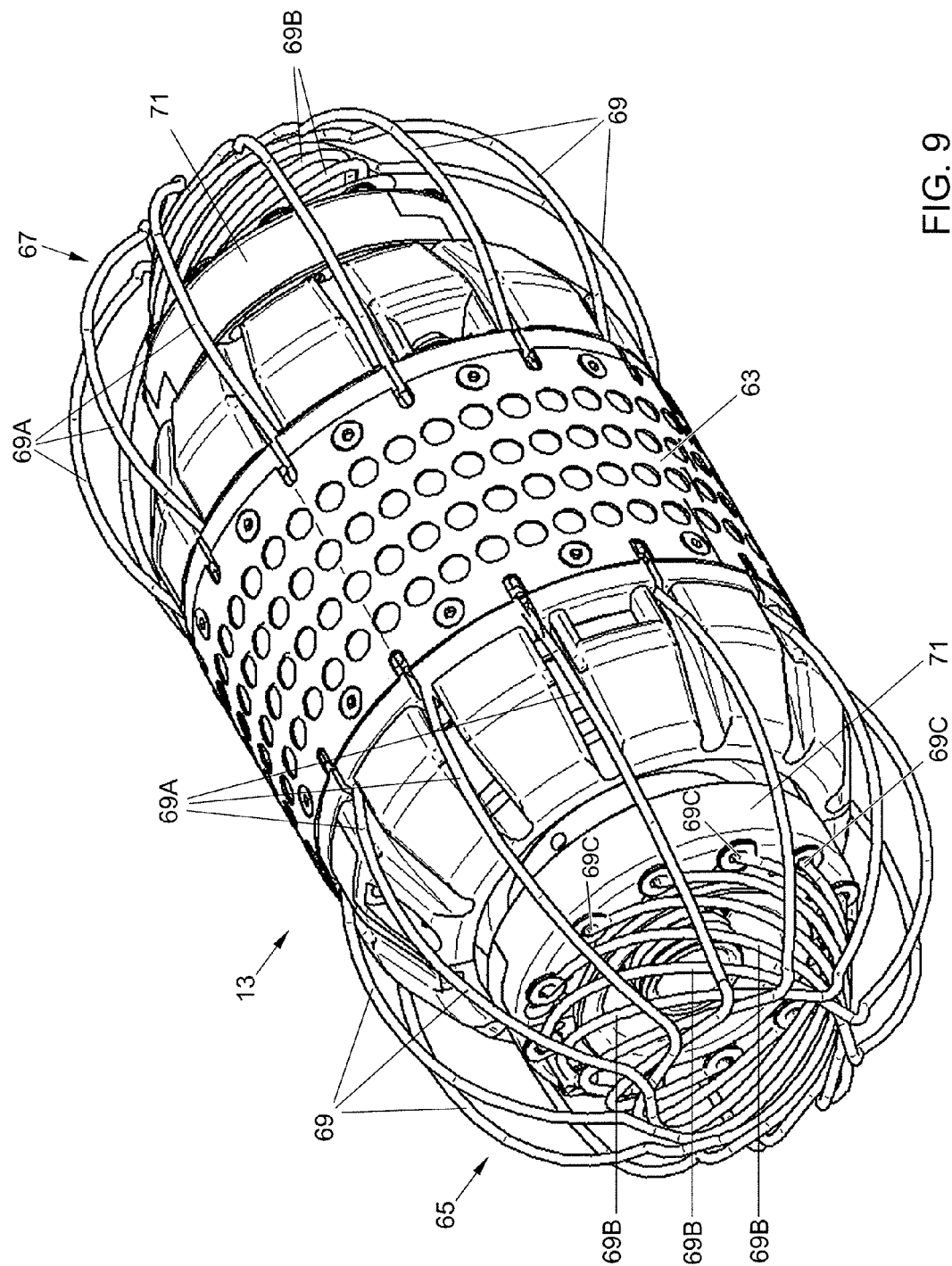
FIG. 9 is a perspective view of an ultrasonic testing module suitable for use in the tool of FIG. 1, with its centering springs compressed for a small diameter pipe.
Figure 10:
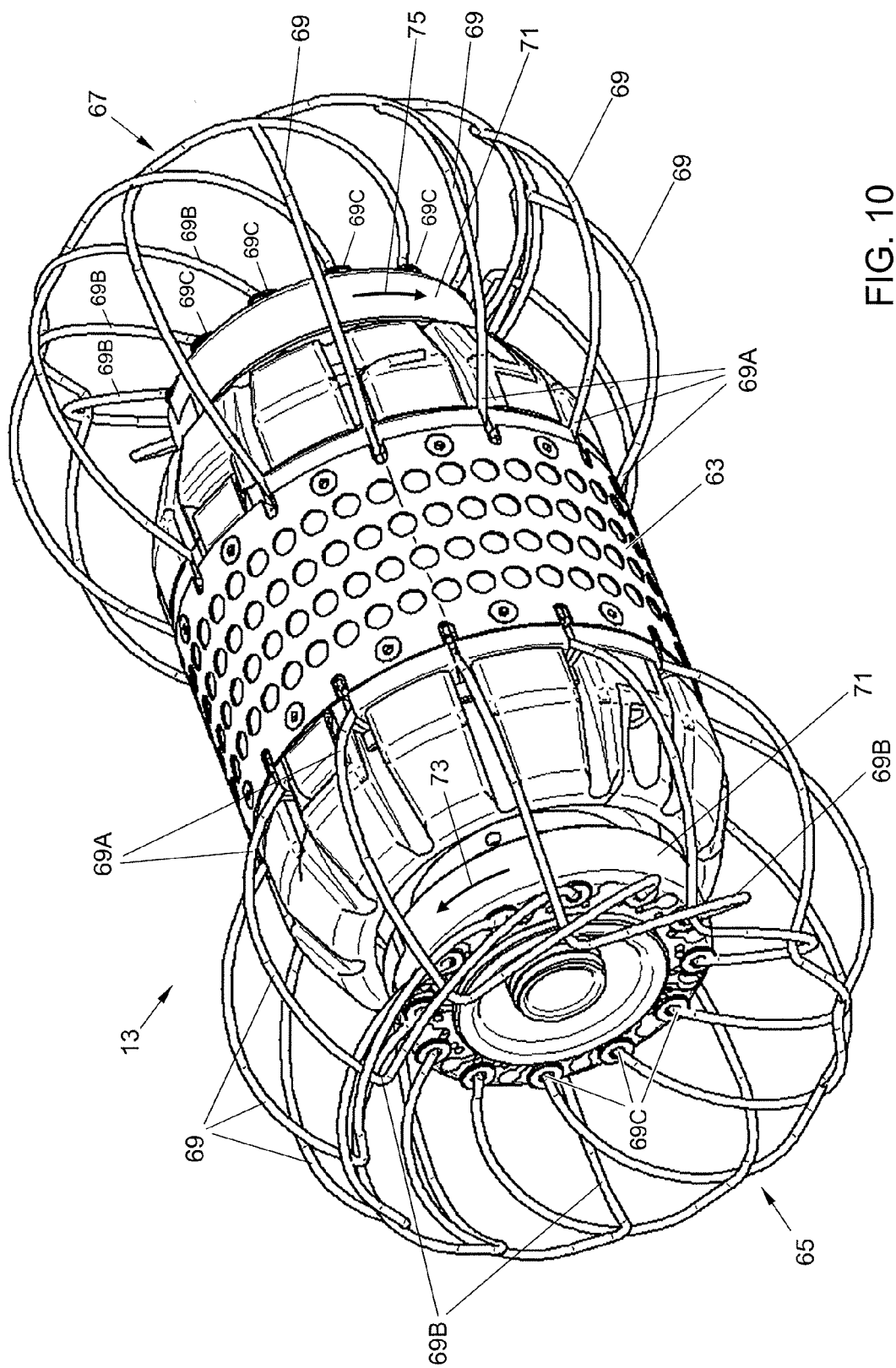
FIG. 10 is a perspective view of the ultrasonic testing module of FIG. 9, with its centering springs expanded for a larger diameter pipe.

The ultrasonic testing module 13, shown in FIGS. 9 and 10 can be of a type as described in U.S. Pat. No. 7,950,284 and the ultrasonic transducers and part of the electronics can be housed in a body 63. The body 63 is kept aligned with the pipeline axis by first and second sets of wire-springs 65, 67. Each set of wire-springs 65, 67 includes a plurality of wire-springs 69. The wire-springs 69 are each generally curved and have an end of a first wire-springs part 69A pivotally connected to an outer circumference of the body 63 and an end 69C of a second wire spring part 69B pivotally connected to a rotatable ring 71 on a relevant axial end of the ultrasonic testing module 13. The bias of the wire-springs 69 is such that the rotatable rings 71 are rotated in the direction of arrows 73 and 75 as indicated in FIG. 10, which causes the wire-springs 69 to expand as permitted by the inner pipeline diameter. In this example the rings 71 are freely rotating and only moved under the influence of the wire-springs 69. However, when an increased bias would be needed, it is also conceivable that the rings 71 are additionally biased in the direction of arrows 73 and 75 by means of torsion springs within the body 63 of the ultrasonic testing module 13.

FIGS. 9 and 10 thus show the ultrasonic testing module, wire springs 69 in (small diameter pipe, FIG. 9) and out (large diameter pipe, FIG. 10).

The ultrasonic testing (UT) module 13 houses the ultrasonic transducers and part of the electronics. As the tool could rotate (slowly) around its longitudinal axis as it travels through the pipe and it is advantageous during the evaluation of the measurement to know at which circumferential position an indication is located (e.g. corrosion at the bottom side of the pipe) an inclinometer (known, conventional) is integrated in the ultrasonic testing module 13 to register the orientation of the tool during the measurement. Optionally this inclinometer is also used to register the presence of bends and/or the inclination of the pipe axis. Optionally the electronics, or part thereof, for the ultrasonic measurement are positioned in a separate work module. In the present embodiment the ultrasonic testing module 13 contains multiplexer electronics. These electronics are modular, having all the required electronics for a single ring of ultrasonic transducers, and preferably fit within the single ring of ultrasonic transducers.

For reliable ultrasonic measurements of the thickness of the pipe wall, especially when using ultrasonic beams with small dimensions, the ultrasonic testing module 13 must be substantially centralized inside the pipe and substantially aligned with the longitudinal axis of the pipe to maintain substantially perpendicular incidence of the ultrasonic beams on the pipe surface. In addition, the ultrasonic testing module 13 must be maintain substantially aligned with the longitudinal pipe axis, so pitching (tilt forward and backward) and yawing (swivel left and right) must be minimized. For detection and sizing of cracks in the wall of the pipeline or welds connecting pipe segments the ultrasonic beams are not necessarily perpendicular to the pipe wall, however also in this case the ultrasonic testing module 13 must be substantially centralized inside the pipe and be kept substantially aligned with the longitudinal axis of the pipe to maintain well defined beam angles at the pipe wall. To achieve this, for a range of diameters, the ultrasonic testing module is centralized and aligned with two sets of springs 65, 67, one set on each end of the module 13. For each set of springs 65, 67 the outer diameter enclosing the individual springs 69 in contact with the pipe inner diameter is always concentric with the longitudinal axis of the ultrasonic testing module 13. This is achieved by connecting one end 69A of each spring 69 with the body 63 of the ultrasonic testing module 13 and the other end 69C of each spring 69 to the rotating ring 71 that can optionally be spring loaded with a torsion spring (not shown, but conventional). Due to the present design and assembly, the tension in the springs 69 is large enough to force the springs 69 outwards, counteracting the weight of the ultrasonic module 13 and the possible forces in the interconnection due to the weight of other modules. On the other hand, the force pushing the springs 69 outwards shall not be too high and shall allow for compression of the springs 69 when the ultrasonic module 13 enters into a smaller diameter pipe. In addition the tension of an optional additional torsion spring, when used, should be not too high to limit the amount of friction between the springs 69 and the inside surface of the pipe.

A side view of an individual wire-spring 69 is shown in FIG. 11A. It is clearly seen that the first wire-spring part 69A is curved in the plane of the drawing. The second wire-spring part 69B appears substantially straight in a plane perpendicular to the plane of the drawing. FIG. 11B is a side view of the wire-spring perpendicular to the side view of FIG. 11A. In FIG. 11B the second wire-spring part 69B now is seen to be curved in the plane of the drawing while the first wire-spring part 69A now is shown substantially straight. FIG. 11C is an end elevation of the wire-spring 69, which again shows first wire-spring part 69A as substantially straight in the plane of the drawings and also allows to recognize the curvature of the second wire-spring part 69B. This form is caused by a substantially 90° bend 77 between the curved first and second wire-spring parts 69A and 69B. The first curved spring part 69A is provided with and end hook 79 (FIG. 11A) for pivotal connection to the body 63 of the ultrasonic testing module 13. The second curved wire-spring part 69B at an end opposite to the 90° bend 77 terminates in a further 90° bend 81 to form the wire-spring end 69C.

The outer part of the wire springs (69A, see FIGS. 11A-C) is curved such that always a part of the wire spring remains in contact with the pipe inner surface for a variety of pipe diameters. Also, the curvature of wire spring part 69A allows smooth passing of obstacles at the inner surface of the pipe, such as weld penetrations, in both travelling directions. The wire spring part 69A of the spring is connected to the body 63 of the ultrasonic testing module 13 and maintains substantially in a plane through the axis of the body 63 in a radial direction. This also limits the possible rotation of the module 13 when the set of springs 65, 67 adapt to a different diameter.

The wire spring part 69B of the spring 69 is connected to the rotating ring 71 and must be positioned on the ring 71 in such a way that the ring 71 is rotated when a pressure is applied on the outside of the set of springs 65, 67 due to a reduction in diameter of the pipe. As a result the maximum rotation of the rotating ring 71 will be less than half the circumference, typically about one third.

It should be noted in this regard that the interconnections between the modules must be taken into account for the movement and design of the springs, as the interconnections block the springs from moving too close to the centerline axis of the module body. For tools without interconnections (not part of the present invention), the springs could cross the module axis.

The two curved parts of the spring (69A, 69B) are in two substantially perpendicular planes. One plane extends through the axis of the module (wire spring part 69A), another plane extends perpendicular to the axis of the module (wire spring part 69B).

At the end of wire spring part 69A the spring has a hook 79 to be connected to the body 63 of the ultrasonic testing module 13. The hook 79 is kept in place with a pin for each spring, or a wire for all springs together (the latter option is not shown, but conventional). This configuration allows the outer part of the wire spring (69A) to rotate in radial direction, around the pin or wire, when the spring 69 adapts to pipes of various diameters. Both sides of the hook 79 are flattened to allow smooth rotation of the hook. Both flat surfaces are parallel to the plane of wire spring part 69A. The flattened sides of the hook 79 also prevent point pressure of the spring on sides of the slot in which the hook fits. It should be noted in this regard that the body 63 of the ultrasonic testing module 13 can be made of plastic which could be prone to damage or wear.

At the end of wire spring part 69B the spring is bent so wire spring end 69C is substantially parallel to the plane of wire spring part 69A. Part 69C fits into a hole of the rotating ring 71. If the surface pressure of wire spring end 69C in the rotating ring 71 is too high for the selected materials (e.g. if the rotating ring is made of plastic) then a cylinder (e.g of a metal) around wire spring end 69C can be used to reduce wear.

The end of wire spring end 69C is bent to lock the spring into the rotating ring via a 'keyhole' construction, as will be explained below and to avoid the cylinder, if present, from falling off.

During assembly of the springs to the ultrasonic testing module, the hook at side 69A of the spring is connected to the body of the module. Then for each spring end 69C is fitted into the rotating ring 71 in a hole closest to the hook of that spring 69. In this neutral position there is substantially no tension in the springs 69, which allows for easy and fast assembly. When all springs 69 are mounted the ring 71 is rotated manually, in the direction of the curvature of the spring, wire spring part 69B causing tension in the springs. To prevent the springs from rotating the ring back to the neutral position, a pin and stop block are mounted to the ring and body of the ultrasonic testing module (not shown, but conventional). As a result the tension in the springs 69 tries to rotate the ring 71 back towards the neutral position limited by the stop block, while this rotation of the ring brings wire spring end 69C closer to the hook 79 at wire spring part 69A, resulting in pushing wire spring part 69A outwards.

Hence, this configuration always tries to maximize the diameter of the spring combination, causing the body 63 of the module 13 to be centralized in the pipe for a range of pipe diameters.

The end of the spring at wire spring end 69C is bent to lock the spring to the rotating ring 71 via a 'keyhole' construction. When the ring 71 is rotated away from the neutral position after the springs 69 are mounted, the keyhole configuration prevents this end of the spring 69 from slipping out of the rotating ring 71.

The described set of springs 65, 67 will keep the axis of the module 13 centralized in pipes of a variety of diameters. In case the pipe is not perfectly circular, for example if a dent or obstacle on the inner surface is present, then the module 13 will be positioned in a position that corresponds to equilibrium of all spring forces.

It should be noted in this regard that spring steel is most suitable for manufacturing durable springs. In case the spring force is not enough or in case a different material is selected it could be required to provide spring loaded means to the rotating ring 71 such as a torsion spring.

Alternatively: if the rotating ring 71 is provided with a torsion spring and the connection of the hook 79 to the body 63 of the module 13 would allow for some sideways rotation, then the spring could be replaced by a similar shape made from solid, non-deformable material.

This tool is intended for pipelines for transport of fluids, such as water, oil and like products, that are difficult to inspect, both on-shore and off-shore.

It is to be noted that from a mechanical point of view this tool can also be used in pipelines for gas transport, however then a suitable measurement method must be applied.

In addition, difficult to inspect pipes can also be present at refineries, chemical and other hydrocarbon industries. Also the power industry has piping systems that require such solutions.

The skilled person will also perceive that the encoder module and ultrasonic testing module described herein can also be made part of different tools for in-line inspection or treatment, or be combined with different traction modules.

Thus a tool, method, and system for in-line inspection or treatment of a pipeline are described, with the tool 1 including a first traction module 3A on a first longitudinal end, and a second traction module 3B on a second end. The tool 1 further includes at least one work module, such as an encoder module 5 and/or an ultrasonic testing module 13, which is positioned between the first and second traction modules 3A, 3B. A plurality of flexible connecting elements 7, 11 each interconnect one of the first and second traction modules 3A, 3B for articulation to the at least one work module. Each of the first and second traction modules 3A, 3B has at least one sealing element 29A that causes propulsion in response to a fluid flow in a pipeline to be inspected or treated in one direction and allows relatively unhindered passing of the fluid flow in an opposite direction. The at least one sealing element 29A of the first traction module 3A has an orientation functionally opposite to the at least one sealing element 29A of the second traction module 3B.

It is thus believed that the operation and construction of the present invention will be apparent from the foregoing description and drawings appended thereto. For the purpose of clarity and a concise description features are described herein as part of the same or separate embodiments, however, it will be appreciated that the scope of the invention may include embodiments having combinations of all or some of the features described. It will be clear to the skilled person that the invention is not limited to any embodiment herein described and that modifications are possible which may be considered within the scope of the appended claims. Also kinematic inversions are considered inherently disclosed and can be within the scope of the invention. In the claims, any reference signs shall not be construed as limiting the claim. The term 'comprising' and 'including' when used in this description or the appended claims should not be construed in an exclusive or exhaustive sense but rather in an inclusive sense. Thus the expression 'comprising' as used herein does not exclude the presence of other elements or steps in addition to those listed in any claim. Furthermore, the words 'a' and 'an' shall not be construed as limited to 'only one', but instead are used to mean 'at least one', and do not exclude a plurality. Features that are not specifically or explicitly described or claimed may be additionally included in the structure of the invention without departing from its scope. Expressions such as: "means for . . . " should be read as: "component configured for . . . " or "member constructed to . . . " and should be construed to include equivalents for the structures disclosed. The use of expressions like: "critical", "preferred", "especially preferred" etc. is not intended to limit the invention. Additions, deletions, and modifications within the purview of the skilled person may generally be made without departing from the scope of the invention, as determined by the claims.

The invention claimed is:

1. A tool for in-line inspection of a pipeline, including:
   first and second longitudinal ends;
   a first traction module on the first longitudinal end;
   a second traction module on the second end;
   at least one work module positioned between the first and second traction modules; and
   a plurality of flexible connecting elements each interconnecting one of the first and second traction modules for articulation to the at least one work module;
   wherein the first traction module comprises a first sealing element and the second traction module comprises a second sealing element;
   wherein each of the first sealing element and the second sealing element is adapted to cause propulsion in response to a fluid flow in a pipeline to be inspected or treated in one direction and to allow unhindered passing of the fluid flow in an opposite direction without external intervention by an operator, and wherein the first sealing element of the first traction module has an orientation functionally opposite to the second sealing element of the second traction module;
   wherein the second sealing element of the second traction module allows the fluid flow to pass, while the first sealing element of the first traction module is effective to move the tool in one fluid flow direction, and vice versa in an opposite fluid flow direction, such that traction is only by the respective sealing element that is leading in a direction of movement of the tool;
   wherein the first sealing element includes a rigid disc on a side remote from the at least one work module, and a flexible disc on a side that faces the at least one work module; wherein at least one of the first and second traction modules includes a third sealing element in addition to the first or second sealing element, which the third sealing element is adapted to cause propulsion in response to a fluid flow in a pipeline to be inspected in the same direction as the first or second sealing element; and
   wherein the at least one work module is an ultrasonic testing module; an encoder module; a multiplexer module; an electronics module of any combination of a pulser, a receiver, a digitizer and a data storage; or a battery module; or a combination thereof.

2. The tool according to claim 1, wherein the third sealing element is positioned on a side of the first or second sealing element facing the at least one work module, and is spaced therefrom at a distance, which in length corresponds to a diameter dimension of the first or second sealing element.

3. The tool according to claim 1, wherein the third sealing element is flexibly connected to the first or second sealing element by a flexible connection.

4. The tool according to claim 3, wherein the flexible connection has an inherent bias to return to a straight configuration.

5. The tool according to claim 3, wherein the flexible connection includes an elongate helical spring surrounded by an elongate metal covering, which is flexible but capable of transmitting traction forces.

6. The tool according to claim 1, wherein an outer end of at least one of the first and second traction modules, on a side of the first or second sealing element remote to the at least one work module, has a nose cone.

7. The tool according to claim 6, wherein the nose cone has a rounded tip.

8. The tool according to claim 6, wherein the nose cone has a hollow interior arranged for accommodating items of equipment.

9. The tool according to claim 6, wherein the nose cone has a longitudinal length that does not exceed a value of $\sqrt{(D^2/4+R*D)}$, in which D is an inner diameter of a pipeline to be inspected, and R is a radius of curvature of a smallest bend in a pipeline to be inspected or treated.

10. The tool according to claim 1, wherein the rigid disc has radially extending tongues, wherein the flexible disc has radially extending slits, and wherein the radially extending tongues at least partially overlap with the radially extending slits.

11. The tool according to claim 1, wherein the flexible disc has a diameter that is equal to or smaller than a largest or average diameter of a pipeline to be inspected or treated by the tool.

12. The tool according to claim 1, wherein the rigid disc has a diameter that is smaller than a smallest diameter of a pipeline to be inspected or treated by the tool, by an amount exceeding a thickness of the flexible disc.

13. The tool according to claim 1, wherein each of the plurality of flexible connecting elements includes an elongate helical spring surrounded by an elongate metal covering, which is flexible but capable of transmitting traction forces, and wherein at least one concentric bristle is connected around one longitudinal end of the elongate metal covering.

14. The tool according to claim 13, wherein a flexible tubular hose is interposed between the elongate helical spring and the elongate flexible metal covering.

15. The tool according to claim 13, wherein a further concentric bristle is connected around an opposite longitudinal end of the elongate metal covering.

16. The tool according to claim 1, wherein the at least one work module is an encoder module arranged for measuring a travel distance of the tool in a pipeline to be inspected or treated by the tool.

17. The tool according to claim 16, wherein the encoder module has a cylindrical body and at least one encoder wheel is mounted on an axially extending leaf-spring for movement between a radially innermost and a radially outermost position with respect to the body.

18. The tool according to claim 17, wherein the axially extending leaf-spring provides an outward bias to the at least one encoder wheel.

19. The tool according to claim 17, wherein opposite ends of the axially extending leaf-spring are each pivotally connected to a confronting axial part of the cylindrical body.

20. The tool according to claim 17, wherein an additional covering leaf extends laterally from each opposite side of the axially extending leaf-spring, to prevent the encoder wheel from extending too deeply into off-takes at pipe junctions of a pipeline to be inspected or treated by the tool.

21. The tool according to claim 17, wherein the structure of the encoder wheel mounted on an axially extending leaf-spring for radial movement between innermost and outermost positions is duplicated on a diametrically opposite side the body.

22. The tool according to claim 1, wherein the at least one work module is an ultrasonic testing module arranged for determining wall thickness of or cracks in the wall of a pipeline to be inspected or treated by the tool.

23. The tool according to claim 22, wherein the ultrasonic testing module includes an elongate cylindrical housing for accommodating any one of transducers and multiplexers, and at least one set of centering springs on a first axial end of the cylindrical housing, at least one set of centering springs includes a plurality of radially expanding wire springs.

24. The tool according to claim 23, wherein each wire spring has a first part axially extending with respect to the cylindrical housing, having a free end pivotally connected to an outer circumference of the cylindrical housing, and a radially extending second part with an end part pivotally connected to a rotatable ring on the first axial end of the cylindrical housing.

25. The tool according to claim 24, wherein the axially extending first part and the radially extending second part of each wire spring are connected by a right-angle bend.

26. The tool according to claim 24, wherein the axially extending first part and the radially extending second part of each wire spring are curved.

27. The tool according to claim 26, wherein the axially extending first part is outwardly curved to define an enclosing outer contact diameter that corresponds to an inner diameter of a pipeline to be inspected or treated by the tool, thereby ensuring that a longitudinal axis of the cylindrical housing is concentric with the inner pipeline diameter.

28. The tool according to claim 23, wherein the structure of a set of centering springs including a plurality of radially expanding wire springs, each having an axially extending first part pivotally connected to the cylindrical housing, and a radially extending second part connected to a rotatable ring, is duplicated on an opposite second axial end of the cylindrical housing.

29. The tool according to claim 22, wherein the ultrasonic testing module is pressure compensated by an oil filling.

30. An ultrasonic testing module for an in-line inspection tool of claim 1, arranged fear determining wall thickness of or cracks in the wall of a pipeline to be inspected or treated by the tool, wherein the ultrasonic testing module includes an elongate cylindrical housing for accommodating any one of transducers and multiplexers, and at least one set of centering springs on a first axial end of the cylindrical housing, at least one set of centering springs includes a plurality of radially expanding wire springs.

31. The ultrasonic testing module according to claim 30, wherein each wire spring has a first part axially extending with respect to the cylindrical housing, having a free end pivotally connected to an outer circumference of the cylindrical housing, and a radially extending second part with an end part pivotally connected to a rotatable ring on the first axial end of the cylindrical housing.

32. The ultrasonic testing module according to claim 31, wherein the axially extending first part and the radially extending second part of each wire spring are connected by a right-angle bend.

33. The ultrasonic testing module according to claim 31, wherein the axially extending first part and the radially extending second part of each wire spring are curved.

34. The ultrasonic testing module according to claim 33, wherein the axially extending first part is outwardly curved to define an enclosing outer contact diameter that corresponds to an inner diameter of a pipeline to be inspected or treated by the tool, thereby ensuring that the cylindrical housing is in the center of the pipeline.

35. The ultrasonic testing module according to claim 30, wherein the structure of a set of centering springs including a plurality of radially expanding wire springs, each having an axially extending first part pivotally connected to the cylindrical housing, and a radially extending second part connected to a rotatable ring, is duplicated on an opposite second axial end of the cylindrical housing.

36. The ultrasonic testing module according to claim 30, wherein the ultrasonic testing module is pressure compensated by an oil filling.

37. A system including a tool according to claim 1, and a pipeline having a longitudinal pipe axis, and at least one bend therein with a radius of curvature of the longitudinal pipe axis that is the same dimension as a diameter of the pipeline at the at least one bend, wherein when at least one of the first and second traction modules is positioned in the at least one bend, the first sealing element of the first traction module or the second sealing element of the second traction module remains perpendicular to the longitudinal pipe axis.

38. The system according to claim 37, wherein an outer end of the relevant at least one first or second traction module, on a side of the first sealing element remote to the at least one work module, has a nose cone that is in contact with an inner surface of an outer wall of the at least one bend.

39. The system according to claim 38, wherein the nose cone has a rounded tip.

40. The system according to claim 38, wherein the nose cone has a longitudinal length that does not exceed a value of $\sqrt{(D^2/4+R*D)}$, in which D is an inner diameter of the pipeline, and R is a radius of curvature of the at least one bend.

41. A method of inspecting a pipeline, including:
providing the tool of claim 1;
introducing the tool into the pipeline;
causing the tool to be propelled in response to a fluid flow generated in the pipeline in a first direction;
collecting and recording data by an ultrasonic testing module with respect to position and wall thickness of or cracks in the wall of the pipeline during propelling in the first direction;
generating a fluid flow opposite to the first direction causing the tool to move in a second direction;
collecting and recording data by the ultrasonic testing module with respect to position and wall thickness of or cracks in the wall of the pipeline during propelling in the second direction;
removing the tool from the pipeline;
retrieving the collected and recorded data from the tool; and
processing and analyzing the collected and recorded data by a computer to determine and identify locations of the pipeline in need of treatment.

42. The tool according to claim 1, wherein the first traction module further comprises a bristle.

43. A tool for in-line inspection of a pipeline, including:
first and second longitudinal ends;
a first traction module on the first longitudinal end;
a second traction module on the second end;
at least one work module positioned between the first and second traction modules; and
a plurality of flexible connecting elements each interconnecting one of the first and second traction modules for articulation to the at least one work module;
wherein the first traction module comprises a first sealing element and the second traction module comprises a second sealing element;
wherein each of the first sealing element and the second sealing element is adapted to cause propulsion in response to a fluid flow in a pipeline to be inspected or treated in one direction and to allow unhindered passing of the fluid flow in an opposite direction without external intervention by an operator, and wherein the first sealing element of the first traction module has an orientation functionally opposite to the second sealing element of the second traction module;
wherein the second sealing element of the second traction module allows the fluid flow to pass, while the first sealing element of the first traction module is effective to move the tool in one fluid flow direction, and vice versa in an opposite fluid flow direction, such that traction is only by the respective sealing element that is leading in a direction of movement of the tool;
wherein the first sealing element includes a rigid disc on a side remote from the at least one work module, and a flexible disc on a side that faces the at least one work module; wherein the rigid disc has a diameter that is equal to or smaller than a diameter of the flexible disc;
wherein at least one of the first and second traction modules includes a third sealing element in addition to the first or second sealing element, which the third sealing element is adapted to cause propulsion in response to a fluid flow in a pipeline to be inspected in the same direction as the first or second sealing element; and
wherein the at least one work module is an ultrasonic testing module; an encoder module; a multiplexer module; an electronics module of any combination of a pulser, a receiver, a digitizer and a data storage; a battery module; or a combination thereof.

\* \* \* \* \*